United States Patent
Bennett et al.

(10) Patent No.: US 6,197,584 B1
(45) Date of Patent: Mar. 6, 2001

(54) ANTISENSE MODULATION OF CD40 EXPRESSION

(75) Inventors: C. Frank Bennett; Lex M. Cowsert, both of Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/071,433

(22) Filed: May 1, 1998

(51) Int. Cl.$^7$ ............................ C12N 15/85; C12N 15/11; C12Q 1/68; C07H 21/04
(52) U.S. Cl. ............................ 435/366; 435/6; 435/325; 435/375; 536/23.1; 536/24.31; 536/24.33; 536/24.5
(58) Field of Search ............................ 435/6, 69.1, 91.1, 435/440, 325, 366, 369, 371, 372, 375, 355, 320.1; 536/23.1, 24.3, 24.31, 24.33, 24.5; 514/44

(56) References Cited

U.S. PATENT DOCUMENTS

| | | | |
|---|---|---|---|
| 5,591,721 | * | 1/1997 | Agrawal et al. .................. 514/44 |
| 5,789,573 | * | 8/1998 | Baker et al. ..................... 536/24.5 |
| 5,877,021 | * | 3/1999 | Stinchcomb et al. ............ 435/366 |

OTHER PUBLICATIONS

Branch, A.D. Tibs 23, Feb. 1998, pp. 45–50.*
Rojanasakul, Y. Advanced Drug Delivery Reviews 18 (Jan. 1996), pp. 115–131.*
Gewirtz, A.M. et al. Proc. Natl. Acad. Sci. USA. vol. 93, pp. 3161–3163, Apr. 1996.*
Agrawal, S. Tibtech. vol. 14. Oct. 1996, pp. 376–387.*
Crooke, S.T. Chapter 1 in "Antisense Research and Application", (ed. Stanley T. Crooke, Springer–Verlag, New York). Jul. 1998, pp. 1–50.*
Milner, N. et al. Nature Biotechnology. vol. 15. Jun. 1997. pp. 537–541.*
Milligan, J.F. et al. J. of Medicinal Chemistry. vol. 36. Jul. 1993, pp. 1923–1937.*
Journal Article:%% Buhlmann et al., "Therapeutic potential for blockade of the CD40 ligand, gp39," *J Clin Immunol*, 16:83–89, 1996.
Journal Article:&& Gruss et al., "CD40/CD40 ligand interactions in normal, reactive and malignant lympho–hematopoietic tissues," *Leuk Lymphoma*, 24:393–422, 1997.
Journal Article:%% Kluth et al., "Endothelial expression of CD40 in renal cell carcinoma," *Cancer Res*, 57:891–899, 1997.

* cited by examiner

*Primary Examiner*—Robert A. Schwartzman
*Assistant Examiner*—Mark L. Shibuya
(74) *Attorney, Agent, or Firm*—Law Offices of Jane Massey Licata

(57) ABSTRACT

Antisense compounds, compositions and methods are provided for modulating the expression of CD40. The compositions comprise antisense compounds, particularly antisense oligonucleotides, targeted to nucleic acids encoding CD40. Methods of using these compounds for modulation of CD40 expression and for treatment of diseases associated with CD40 are provided.

19 Claims, No Drawings

ANTISENSE MODULATION OF CD40 EXPRESSION

FIELD OF THE INVENTION

The present invention provides compositions and methods of modulating the expression of CD40. In particular, this invention relates to antisense compounds, particularly oligonucleotides, specifically hybridizable with nucleic acids encoding human CD40. Such oligonucleotides have been shown to modulate the expression of CD40.

BACKGROUND OF THE INVENTION

The immune system serves a vital role in protecting the body against infectious agents. It is well established, however, that a number of disease states and/or disorders are a result of either abnormal or undesirable activation of immune responses. Common examples include graft versus host disease (GVHD), graft rejection, inflammation, and autoimmune linked diseases such as multiple sclerosis (MS), systemic lupus erythematosus (SLE), and certain forms of arthritis.

In general, an immune response is activated as a result of either tissue injury or infection. Both cases involve the recruitment and activation of a number of immune system effector cells (i.e. B- and T-lymphocytes, macrophages, eosinophils, neutrophils) in a process coordinated through a series of complex cell-cell interactions. A typical scenario by which an immune response is mounted against a foreign protein is as follows: Foreign proteins captured by antigen presenting cells (APC's) such as macrophages or dendritic cells are processed and displayed on the cell surface of the APC. Circulating T-helper cells which express an immunoglobulin that recognizes (i.e. binds) the displayed antigen undergo activation by the APC. These activated T-helpers in turn activate appropriate B-cell clones to proliferate and differentiate into plasma cells that produce and secrete humoral antibodies targeted against the foreign antigen. The secreted humoral antibodies are free to circulate and bind to any cells expressing the foreign protein on their cell surface, in effect marking the cell for destruction by other immune effector cells. In each of the stages described above, direct cell-cell contact between the involved cell types is required in order for activation to occur [Gruss et al., *Leuk. Lymphoma*, 24, 393 (1997)]. In recent years, a number of cell surface receptors that mediate these cell-cell contact dependent activation events have been identified. Among these cell surface receptors is CD40 and its physiological ligand, CD40 Ligand (CD40L).

CD40 was first characterized as a receptor expressed on B-lymphocytes. It was later found that engagement of B-cell CD40 with CD40L expressed on activated T-cells is essential for T-cell dependent B-cell activation (i.e. proliferation, immunoglobulin secretion, and class switching. It was subsequently revealed that functional CD40 is expressed on a variety of cell types other than B-cells, including macrophages, dendritic cells, thymic epithelial cells, Langerhans cells, and endothelial cells. These studies have led to the current belief that CD40 plays a broad role in immune regulation by mediating interactions of T-cells with B-cells as well as other cell types. In support of this notion, it has been shown that stimulation of CD40 in macrophages and dendritic results is required for T-cell activation during antigen presentation [Gruss et al., *Leuk. Lymphoma*, 24, 393 (1997)]. Recent evidence points to a role for CD40 in tissue inflammation as well. Production of the inflammatory mediators IL-12 and nitric oxide by macrophages have been shown to be CD40 dependent [Buhlmann and Noelle, *J. Clin. Immunol.*, 16, 83 (1996)]. In endothelial cells, stimulation of CD40 by CD40L has been found to induce surface expression of E-selectin, ICAM-1, and VCAM-1, promoting adhesion of leukocytes to sites of inflammation [Buhlmann and Noelle, *J. Clin. Immunol.*, 16, 83 (1996); Gruss et al., *Leuk. Lymphoma*, 24, 393 (1997)]. Finally, a number of reports have documented overexpression of CD40 in epithelial and hematopoietic tumors as well as tumor infiltrating endothelial cells, indicating that CD40 may play a role in tumor growth and/or angiogenesis as well [Gruss et al., *Leuk. Lymphoma*, 24, 393 (1997); Kluth et al., *Cancer Res.*, 57, 891 (1997)].

Due to the pivotal role that CD40 plays in humoral immunity, the potential exists that therapeutic strategies aimed at downregulating CD40 may provide a novel class of agents useful in treating a number of immune associated disorders, including but not limited to graft-versus-host disease (GVHD), graft rejection, and autoimmune diseases such as multiple sclerosis (MS), systemic lupus erythematosus (SLE), and certain forms of arthritis. Inhibition of CD40 may also prove useful as an anti-inflammatory compound, and could therefore be useful as treatment for a variety of inflammatory and allergic conditions such as asthma, rheumatoid arthritis, allograft rejections, inflammatory bowel disease, various dermatological conditions, and psoriasis. Finally, as more is learned of the association between CD40 overexpression and tumor growth, inhibitors of CD40 may prove useful as anti-tumor agents and inhibitors of other hyperproliferative conditions as well.

Currently, there are no known therapeutic agents which effectively inhibit the synthesis of CD40. To date, strategies aimed at inhibiting CD40 function have involved the use of a variety of agents that disrupt CD40/CD40L binding. These include monoclonal antibodies directed against either CD40 or CD40L, soluble forms of CD40, and synthetic peptides derived from a second CD40 binding protein, A20. The use of neutralizing antibodies against CD40 and/or CD40L in animal models has provided evidence that inhibition of CD40 stimulation would have therapeutic benefit for GVHD, allograft rejection, rheumatoid arthritis, SLE, MS, and B-cell lymphoma [Buhlmann and Noelle, *J. Clin. Immunol*, 16, 83 (1996)]. However, due to the expense, short half-life and bioavailability problems associated with the use of large proteins as therapeutic agents, there is a long-felt need for additional agents capable of effectively inhibiting CD40 function. Antisense oligonucleotides avoid many of the pitfalls of current agents used to block CD40/CD40L interactions and may therefore prove to be uniquely useful in a number of therapeutic, diagnostic and research applications.

SUMMARY OF THE INVENTION

The present invention is directed to antisense compounds, particularly oligonucleotides, which are targeted to a nucleic acid encoding CD40, and which modulate the expression of CD40. Pharmaceutical and other compositions comprising the antisense compounds of the invention are also provided. Further provided are methods of modulating the expression of CD40 in cells or tissues comprising contacting said cells or tissues with one or more of the antisense compounds or compositions of the invention. Further provided are methods of treating an animal, particularly a human, suspected of having or being prone to a disease or condition associated with expression of CD40 by administering a therapeutically or prophylactically effective amount of one or more of the antisense compounds or compositions of the invention.

DETAILED DESCRIPTION OF THE INVENTION

The present invention employs oligomeric antisense compounds, particularly oligonucleotides, for use in modulating the function of nucleic acid molecules encoding CD40, ultimately modulating the amount of CD40 produced. This is accomplished by providing antisense compounds which specifically hybridize with one or more nucleic acids encoding CD40. As used herein, the terms "target nucleic acid" and "nucleic acid encoding CD40" encompass DNA encoding CD40, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of CD40. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding CD40. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokayotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding CD40, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'—5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a pre-mRNA transcript to yield one or more mature mRNA. The remaining (and therefore translated) regions are known as "exons" and are spliced together to form a continuous mRNA sequence. mRNA splice sites, i.e., exon-exon or intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Targeting particular exons in alternatively spliced mRNAs may also be preferred. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, or in the case of in vitro assays, under conditions in which the assays are performed.

Antisense compounds are commonly used as research reagents and diagnostics. For example, antisense oligonucleotides, which are able to inhibit gene expression with exquisite specificity, are often used by those of ordinary skill to elucidate the function of particular genes, and, in many cases, their relevance to disease processes. This is often referred to as "target validation." Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense oligonucleotides have been employed as drugs in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases. Particularly preferred are antisense oligonucleotides comprising from about 8 to about 30 nucleobases (i.e. from about 8 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalklyphosphotriesters, and boranophosphates having normal 3'–5' linkages, 2'–5' linked analogs of these, and those having inverted polarity wherein the adjacent pairs of nucleoside units are linked 3'–5' to 5'–3' or 2'–5' to 5'–2'. Various salts, mixed salts and free acid forms are also included.

Representative United States patents that teach the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262, each of which is herein incorporated by reference. Further teaching of PNA compounds can be found in Nielsen et al., *Science*, 254, 1497 (1991).

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl, O-, S-, or N-alkenyl, or O-, S- or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$NH$_2$, O($CH_2$)$_n$$CH_3$, O($CH_2$)$_n$ONH$_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, S$CH_3$, OCN, Cl, Br, CN, $CF_3$, O$CF_3$, SO$CH_3$, SO$_2$$CH_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'—O—$CH_2$$CH_2$O$CH_3$, also known as 2'-O-(2-methoxyethyl) or 2'-MOE) [Martin et al., *Helv. Chim. Acta,* 78, 486 (1995)] i.e., an alkoxyalkoxy group. A further preferred modification includes 2'-dimethylaminooxyethoxy, i.e., a 2'-O($CH_2$)$_2$ON($CH_3$)$_2$ group, also known as 2'-DMAOE, as described in U.S. patent application Ser. No. 09/016,520, filed on Jan. 30, 1998, now U.S. Pat. No. 6,127,533, which is commonly owned with the instant application and the contents of which are herein incorporated by reference.

Other preferred modifications include 2'-methoxy (2'—O—$CH_3$), 2'-aminopropoxy (2'—O$CH_2$$CH_2$$CH_2$NH$_2$) and 2'-fluoro (2'-F). Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, certain of which are commonly owned with the instant application, and each of which is herein incorporated by reference, and allowed U.S. patent application Ser. No. 08/468,037 filed on Jun. 5, 1995, U.S. Pat. No. 5,859,221, which is commonly owned with the instant application and is also herein incorporated by reference.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering,* pages 858–859, Kroschwitz, J. I., ed. John Wiley & Sons, 1990, those disclosed by Englisch et al., *Angewandte Chemie, International Edition,* 30, 613 (1991), and those disclosed by Sanghvi, Y. S., Chapter 15, *Antisense Research and Applications,* pages 289–302, Crooke, S. T. and Lebleu, B., ed., CRC Press, 3. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., Antisense Research and Applications, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos.: 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, certain of which are commonly owned with the instant application, and each of which is herein incorporated by reference, and allowed U.S. patent application Ser. No. 08/762,488, filed on Dec. 10, 1996, now U.S. Pat. No. 6,083,923, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety [Letsinger et al., *Proc. Natl. Acad. Sci. USA,* 86, 6553 (1989)], cholic acid [Manoharan et al., *Bioorg. Med. Chem. Lett.,* 4, 1053 (1994)], a thioether, e.g., hexyl-S-tritylthiol [Manoharan et al., *Ann. N.Y. Acad. Sci.,* 660, 306 (1992)]; Manoharan et al., *Bioorg. Med. Chem. Let.,* 3, 2765 (1993)], a thiocholesterol [Oberhauser et al., *Nucl. Acids Res.,* 20, 533 (1992), an aliphatic chain, e.g., dodecandiol or undecyl residues [Saison-Behmoaras et al., *EMBO J.,* 10, 111 (1991); Kabanov et al., *FEBS Lett.,* 259, 327 (1990); Svinarchuk et al., *Biochimie,* 75, 49 (1993)), a phospholipid, e.g., dihexadecyl-rac-glycerol or triethylammonium 1,2-di-O-hexadecyl-rac-glycero-3-H-phosphonate [Manoharan et al., *Tetrahedron Lett.,* 36, 3651 (1995); Shea et al., *Nucl. Acids Res.,* 18, 1990)], a polyamine or a polyethylene glycol chain (Manoharan et al., *Nucleosides & Nucleotides,* 14, 969 (1995)], or adamantane acetic acid [Manoharan et al., *Tetrahedron Lett.,* 36, 3651 (1995)], a palmityl moiety [Mishra et al., *Biochim. Biophys. Acta,* 1264, 229 (1995)], or an octadecylamine or hexylamino-carbonyl-oxycholesterol moiety [Crooke et al., *J. Pharmacol. Exp. Ther.,* 277, 923(1996)].

Representative United States patents that teach the preparation of such oligonucleotide conjugates include, but are not limited to, U.S. Pat. Nos.: 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos.: 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference, and allowed U.S. patent application Ser. No. 08/465,880, filed on Jun. 6, 1995, now U.S. Pat. No. 5,955,589, which is commonly owned with the instant application and also herein incorporated by reference.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules.

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos.: 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.,* 1977, 66:1). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of CD40 is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding CD40, enabling sandwich and other assays to easily be constructed to exploit this fact. Hybridization of the antisense oligonucleotides of the invention with a nucleic acid encoding CD40 can be detected by means known in the art. Such means may include conjugation of an enzyme to the oligonucleotide, radiolabelling of the oligonucleotide or any other suitable detection means. Kits using such detection means for detecting the level of CD40 in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, continuous infusion, subcutaneous, intraperitoneal or intramuscular injection, pulmonary administration, e.g., by inhalation or insufflation, or intrathecal or intraventricular administration. For oral administration, it has been found that oligonucleotides with at least one 2'-substituted ribonucleotide are particularly useful because of their absorption and distribution characteristics. Oligonucleotides with at least one 2'-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions and/or formulations comprising the oligonucleotides of the present invention may also include penetration enhancers in order to enhance the alimentary delivery of the oligonucleotides. Penetration enhancers may be classified as belonging to one of five broad categories, i.e., fatty acids, bile salts, chelating agents, surfactants and non-surfactants [Lee et al., *Critical Reviews in Therapeutic Drug Carrier Systems,* 8, 91 (1991); Muranishi, *Critical Reviews in Therapeutic Drug Carrier Systems,* 7, 1 (1990)]. One or more penetration enhancers from one or more of these broad categories may be included. Penetration enhancers are described in pending U.S. patent application Ser. No. 08/886,829, filed on Jul. 1, 1997, and pending U.S. patent application Ser. No. 08/961,469, filed on Oct. 31, 1997, now U.S. Pat. No. 6,083,923, both of which are commonly owned with the instant application and both of which are herein incorporated by reference.

Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) [Lee et al., *Critical Reviews in Therapeutic Drug Carrier Systems,* 1991, page 92; Muranishi, *Critical Reviews in Therapeutic Drug Carrier Systems,* 7, 1 (1990); El-Hariri et al., *J. Pharm. Pharmacol.* 44, 651 (1992). Examples of some presently preferred fatty acids are sodium caprate and sodium laurate, used singly or in combination at concentrations of 0.5 to 5%.

Preferred penetration enhancers are disclosed in pending U.S. patent application Ser. No. 08/886,829, filed on Jul. 1, 1997, which is commonly owned with the instant application and which is herein incorporated by reference.

The physiological roles of bile include the facilitation of dispersion and absorption of lipids and fat-soluble vitamins (Brunton, Chapter 38 In: *Goodman & Gilman's The Pharmacological Basis of Therapeutics,* 9th Ed., Hardman et al., eds., McGraw-Hill, New York, N.Y., 1996, pages 934–935). Various natural bile salts, and their synthetic derivatives, act as penetration enhancers. Thus, the term "bile salt" includes any of the naturally occurring components of bile as well as any of their synthetic derivatives. Preferred bile salts are described in pending U.S. patent application Ser. No. 08/886,829, filed on Jul. 1, 1997, which is commonly owned with the instant application and which is herein incorporated by reference. A presently preferred bile salt is chenodeoxycholic acid, sodium salt (CDCA)(Sigma Chemical Company, St. Louis, Mo.), generally used at concentrations of 0.5 to 2%.

Complex formulations comprising one or more penetration enhancers may be used. For example, bile salts may be used in combination with fatty acids to make complex formulations. Preferred combinations include CDCA combined with sodium caprate or sodium laurate (generally 0.5 to 5%).

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) [Lee et al., *Critical Reviews in Therapeutic Drug Carrier Systems,* 1991, page 92; Muranishi, *Critical Reviews in Therapeutic Drug Carrier Systems,* 7, 1 (1990); Buur et al., *J. Control Rel.,* 14 (1990)]. Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., *Critical Reviews in Therapeutic Drug Carrier Systems,* 1991, page 92); and perfluorochemical emulsions, such as FC-43 (Takahashi et al., *J. Pharm. Phamacol.,* 1988, 40:252).

Non-surfactants include, for example, unsaturated cyclic ureas, 1-alkyl- and 1-alkenylazacyclo-alkanone derivatives (Lee et al., *Critical Reviews in Therapeutic Drug Carrier Systems,* 1991, page 92); and non-steroidal anti-inflammatory agents such as diclofenac sodium, indomethacin and phenylbutazone (Yamashita et al., *J. Pharm. Pharmacol.,* 1987, 39:621).

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioated oligonucleotide in hepatic tissue is reduced when it is coadministered with polyinosinic acid, dextran sulfate, polycytidic acid or 4-acetamido-4'-isothiocyano-stilbene-2,2'-disulfonic acid [Miyao et al., *Antisense Res. Dev.,* 5, 115 (1995); Takakura et al., *Antisense & Nucl. Acid Drug Dev.,* 6, 177 (1996)].

In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinyl-pyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the antisense compounds of the invention are introduced into a patient, colloidal dispersion systems may be used as delivery vehicles to enhance the in vivo stability of the compounds and/or to target the compounds to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layer(s) made up of lipids arranged in a bilayer configuration (see, generally, Chonn et al., Current Op. Biotech., 1995, 6, 698). An example of liposome preparation is described in pending U.S. patent application Ser. No. 08/961,469, filed on Oct. 31, 1997, now U.S. Pat. No. 6,083,923, which is commonly owned with the instant application and which is herein incorporated by reference.

Certain embodiments of the invention provide for liposomes and other compositions containing (a) one or more antisense compounds and (b) one or more other chemotherapeutic agents which function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine, 5-fluorouracil (5-FU), floxuridine (5-FUdR), methotrexate, colchicine, vincristine, vinblastine, etoposide, teniposide, cisplatin and diethylstilbestrol (DES). See, generally, The Merck Manual of Diagnosis and Therapy, 15th Ed., Berkow et al., eds., 1987, Rahway, N.J., pages 1206–1228). Antiinflammatory drugs, including but not limited to nonsteroidal antiinflammatory drugs and corticosteroids, and antiviral drugs, including but not limited to ribivirin, vidarabine, acyclovir and ganciclovir, may also be combined in compositions of the invention. See, generally, The Merck Manual of Diagnosis and Therapy, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Examples of antisense oligonucleotides include, but are not limited to, those directed to the following targets as disclosed in the indicated U.S. Patents, or pending U.S. applications, which are commonly owned with the instant application and are hereby incorporated by reference, or the indicated published PCT applications: raf (WO 96/39415, WO 95/32987 and U.S. Pat. Nos. 5,563,255, issued Oct. 8, 1996, and 5,656,612, issued Aug. 12, 1997), the pl20 nucleolar antigen (WO 93/17125 and U.S. Pat. No. 5,656,743, issued August 12, 1997), protein kinase C (WO 95/02069, WO 95/03833 and WO 93/19203), multidrug resistance-associated protein (WO 95/10938 and U.S. Pat. No. 5,510,239, issued Mar. 23, 1996), subunits of transcription factor AP-1 (pending application U.S. Ser. No. 08/837,201, filed Apr. 14, 1997) now U.S. Pat. No. 5,985,558, Jun kinases (application U.S. Ser. No. 08/910,629, filed Aug. 13, 1997 now U.S. Pat. No. 5,877,309), MDR-1 (multidrug resistance glycoprotein; application U.S. Ser. No. 08/731,199, filed Sep. 30, 1997 now abandoned), HIV (U.S. Pat. Nos. 5,166,195, issued Nov. 24, 1992 and 5,591,600, issued Jan. 7, 1997), herpesvirus (U.S. Pat. No. 5,248,670, issued Sep. 28, 1993 and U.S. Pat. No. 5,514,577, issued May 7, 1996), cytomegalovirus (U.S. Pat. Nos. 5,442,049, issued Aug. 15, 1995 and 5,591,720, issued Jan. 7, 1997), papillomavirus (U.S. Pat. No. 5,457,189, issued Oct. 10, 1995), intercellular adhesion molecule-1 (ICAM-1) (U.S. Pat. No. 5,514,788, issued May 7, 1996), 5-lipoxygenase (U.S. Pat. No. 5,530,114, issued Jun. 25, 1996) and influenzavirus (U.S. Pat. No. 5,580,767, issued Dec. 3, 1996). Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-Alkoxy Amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research*, 21, 3197 (1993)] using commercially available phosphoramidites (Glen Research, Inc., Sterling Va. or ChemGenes, Needham Mass.).

2'-Fluoro amidites

2'-Fluorodeoxyadenosine amidites

2'-fluoro oligonucleotides were synthesized as described previously [Kawasaki, et. al., *J. Med. Chem.*, 36, 831 (1993)] and U.S. Pat. No. 5,670,633, herein incorporated by reference. Briefly, the protected nucleoside $N^6$-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$- displacement of a 2'-beta-trityl group. Thus $N^6$-benzoyl-9-beta-D-arabinofuranosyladenine was selectively protected in moderate yield as the 3',5'-ditetrahydropyranyl (THP) intermediate. Deprotection of the THP and $N^6$-benzoyl groups was accomplished using standard methodologies and standard methods were used to obtain the 5'-dimethoxytrityl- (DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyrylarabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'-phosphoramidites.

2'-Fluorodeoxycytidine

2'-deoxy-2'-fluorocytidine was synthesized via amination of 2'-deoxy-2'-fluorouridine, followed by selective protection to give $N^4$-benzoyl-2'-deoxy-2'-fluorocytidine. Standard procedures were used to obtain the 5'-DMT and 5'-DMT-3'phosphoramidites.

2'-O-(2-Methoxyethyl) modified amidites

2'- O-Methoxyethyl-substituted nucleoside amidites are prepared as follows, or alternatively, as per the methods of Martin, P., *Helvetica Chimica Acta*, 78, 486 (1995).

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–40° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL) The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in CHCl$_3$ (800 mL) and extracted with 2×200 mL of saturated sodium bicarbonate and 2×200 mL of saturated NaCl. The water layers were back extracted with 200 mL of CHCl$_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in CH$_3$CN (700 mL) and set aside. Triethylamine (189 mL, 1.44 M) was added to a solution of triazole (90 g, 1.3 M) in CH$_3$CN (1 L), cooled to −5° C. and stirred for 0.5 h using an overhead stirrer. POCl$_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N$^4$-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/Hexane (1:1) containing 0.5% Et$_3$NH as the eluting solvent. The pure product fractions were evaporated to give 90 g (90%) of the title compound.

N$^4$-Benzoyl-2'-O-methoxyethyl-5'-O-dimethoxytrityl-5-methylcytidine-3'-amidite N$^4$-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOA\Hexane (3:1) as the eluting solvent. The pure fractions were combined to give 90.6 g (87%) of the title compound.

2'-(Aminooxyethyl) nucleoside amidites and 2'-(dimethylaminooxyethyl) nucleoside amidites Aminooxyethyl and dimethylaminooxyethyl amidites are prepared as per the methods of U.S. non provisional application serial No. 60/037,143, filed Feb. 14, 1998, and U.S. Ser. No. 09/016,520, filed Jan. 30, 1998, now U.S. Pat. No. 6,127,533, each of which is commonly owned with the instant application and is herein incorporated by reference.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide (Beaucage reagent) in acetonitrile for the stepwise thiation of the phosphite linkages. The thiation wait step was increased to 68 sec and was followed by the capping step. After cleavage from the controlled pore glass column and deblocking in concentrated ammonium hydroxide at 55° C. (18 hr), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378, 825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAS) are prepared in accordance with any of the various procedures referred to in Peptide Nucleic Acids (PNA): Synthesis, Properties and Potential Applications, *Bioorganic & Medicinal Chemistry*, 4, 5 (1996). They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers."

[2'-O-Me]—[2'-deoxy]—[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 Ammonia/Ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligonucleotide recovered is then analyzed spectrophotometrically for yield and for purity by capillary electrophoresis and by mass spectrometer.

[2'-O-(2-Methoxyethyl)]—[2'-deoxy]—[2'-O-(Methoxyethyl)] Chimeric Phosphorothioate Oligonucleotides

[2'-O-(2-methoxyethyl)]—[2'-deoxy]—[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]—[2'-deoxy Phosphorothioate]—[2'-O-(2-Methoxyethyl) Phosphodiester] Chimeric Oligonucleotide

[2'-O-(2-methoxyethyl phosphodiester]—[2'-deoxy phosphorothioate]—[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al., *J. Biol. Chem.* 266, 18162 (1991). Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman MDQ) or, for individually prepared samples, on a commercial CE apparatus (e.g., Beckman 5000, ABI 270). Base and backbone composition was confirmed by mass analysis of the compounds utilizing Electrospray-Mass Spectroscopy. All assay test plates were diluted from the master plate using single and multi-channel robotic pipettors. Plates were judged to be acceptable if at least 85% of the compounds on the plate were at least 85% full length.

Example 9

Antisense Sequences Targeted to Human CD40

In accordance with the present invention, a series of antisense sequences were designed to target different regions of the human CD40 mRNA, using published sequences [Stamenkovic et al., *EMBO J.*, 8, 1403 (1989); GenBank on number X60592]. The sequences are shown in Table 1.

TABLE 1

Antisense sequences targeted to human CD40 mRNA

| ISIS# | TARGET REGION | TARGET SITE[1] | SEQUENCE | SEQ ID NO. |
|---|---|---|---|---|
| 18623 | 5' UTR | 18 | CCAGGCGGCAGGACCACT | 1 |
| 18624 | 5' UTR | 20 | GACCAGGCGGCAGGACCA | 2 |
| 18625 | 5' UTR | 26 | AGGTGAGACCAGGCGGCA | 3 |
| 18626 | AUG | 48 | CAGAGGCAGACGAACCAT | 4 |
| 18627 | Coding | 49 | GCAGAGGCAGACGAACCA | 5 |
| 18628 | Coding | 73 | GCAAGCAGCCCCAGAGGA | 6 |
| 18629 | Coding | 78 | GGTCAGCAGCAGCCCCA | 7 |
| 18630 | Coding | 84 | GACAGCGGTCAGCAAGCA | 8 |
| 18631 | Coding | 88 | GATGGACAGCGGTCAGCA | 9 |
| 18632 | Coding | 92 | TCTGGATGGACAGCGGTC | 10 |
| 18633 | Coding | 98 | GGTGGTTCTGGATGGACA | 11 |
| 18634 | Coding | 101 | GTGGGTGGTTCTGGATGG | 12 |
| 18635 | Coding | 104 | GCAGTGGGTGGTTCTGGA | 13 |
| 18636 | Coding | 152 | CACAAAGAACAGCACTGA | 14 |
| 18637 | Coding | 156 | CTGGCACAAAGAACAGCA | 15 |
| 18638 | Coding | 162 | TCCTGGCTGGCACAAAGA | 16 |

TABLE 1-continued

Antisense sequences targeted to human CD40 mRNA

| ISIS# | TARGET REGION | TARGET SITE[1] | SEQUENCE | SEQ ID NO. |
|---|---|---|---|---|
| 18639 | Coding | 165 | CTGTCCTGGCTGGCACAA | 17 |
| 18640 | Coding | 176 | CTCACCAGTTTCTGTCCT | 18 |
| 18641 | Coding | 179 | TCACTCACCAGTTTCTGT | 19 |
| 18642 | Coding | 185 | GTGCAGTCACTCACCAGT | 20 |
| 18643 | Coding | 190 | ACTCTGTGCAGTCACTCA | 21 |
| 18644 | Coding | 196 | CAGTGAACTCTGTGCAGT | 22 |
| 18645 | Coding | 205 | ATTCCGTTTCAGTGAACT | 23 |
| 18646 | Coding | 211 | GAAGGCATTCCGTTTCAG | 24 |
| 18647 | Coding | 222 | TTCACCGCAAGGAAGGCA | 25 |
| 18648 | Coding | 250 | CTCTGTTCCAGGTGTCTA | 26 |
| 18649 | Coding | 267 | CTGGTGGCAGTGTGTCTC | 27 |
| 18650 | Coding | 286 | TGGGGTCGCAGTATTTGT | 28 |
| 18651 | Coding | 289 | GGTTGGGGTCGCAGTATT | 29 |
| 18652 | Coding | 292 | CTAGGTTGGGGTCGCAGT | 30 |
| 18653 | Coding | 318 | GGTGCCCTTCTGCTGGAC | 31 |
| 18654 | Coding | 322 | CTGAGGTGCCCTTCTGCT | 32 |
| 18655 | Coding | 332 | GTGTCTGTTTCTGAGGTG | 33 |
| 18656 | Coding | 334 | TGGTGTCTGTTTCTGAGG | 34 |
| 18657 | Coding | 345 | ACAGGTGCAGATGGTGTC | 35 |
| 18658 | Coding | 348 | TTCACAGGTGCAGATGGT | 36 |
| 18659 | Coding | 360 | GTGCCAGCCTTCTTCACA | 37 |
| 18660 | Coding | 364 | TACAGTGCCAGCCTTCTT | 38 |
| 18661 | Coding | 391 | GGACACAGCTCTCACAGG | 39 |
| 18662 | Coding | 395 | TGCAGGACACAGCTCTCA | 40 |
| 18663 | Coding | 401 | GAGCGGTGCAGGACACAG | 41 |
| 18664 | Coding | 416 | AAGCCGGGCGAGCATGAG | 42 |
| 18665 | Coding | 432 | AATCTGCTTGACCCCAAA | 43 |
| 18666 | Coding | 446 | GAAACCCTGTAGCAATC | 44 |
| 18667 | Coding | 452 | GTATCAGAAACCCCTGTA | 45 |
| 18668 | Coding | 463 | GCTCGCAGATGGTATCAG | 46 |
| 18669 | Coding | 468 | GCAGGGCTCGCAGATGGT | 47 |
| 18670 | Coding | 471 | TGGGCAGGGCTCGCAGAT | 48 |
| 18671 | Coding | 474 | GACTGGGCAGGGCTCGCA | 49 |
| 18672 | Coding | 490 | CATTGGAGAAGAAGCCGA | 50 |
| 18673 | Coding | 497 | GATGACACATTGGAGAAG | 51 |
| 18674 | Coding | 500 | GCAGATGACACATTGGAG | 52 |
| 18675 | Coding | 506 | TCGAAAGCAGATGACACA | 53 |
| 18676 | Coding | 524 | GTCCAAGGGTGACATTTT | 54 |
| 18677 | Coding | 532 | CACAGCTTGTCCAAGGGT | 55 |
| 18678 | Coding | 539 | TTGGTCTCACAGCTTGTC | 56 |
| 18679 | Coding | 546 | CAGGTCTTTGGTCTCACA | 57 |
| 18680 | Coding | 558 | CTGTTGCACAACCAGGTC | 58 |
| 18681 | Coding | 570 | GTTTGTGCCTGCCTGTTG | 59 |
| 18682 | Coding | 575 | GTCTTGTTTGTGCCTGCC | 60 |
| 18683 | Coding | 590 | CCACAGACAACATCAGTC | 61 |
| 18684 | Coding | 597 | CTGGGGACCACAGACAAC | 62 |
| 18685 | Coding | 607 | TCAGCCGATCCTGGGGAC | 63 |
| 18686 | Coding | 621 | CACCACCAGGGCTCTCAG | 64 |
| 18687 | Coding | 626 | GGGATCACCACCAGGGCT | 65 |
| 18688 | Coding | 657 | GAGGATGGCAAACAGGAT | 66 |
| 18689 | Coding | 668 | ACCAGCACCAAGAGGATG | 67 |
| 18690 | Coding | 679 | TTTTGATAAAGACCAGCA | 68 |
| 18691 | Coding | 703 | TATTGGTTGGCTTCTTGG | 69 |
| 18692 | Coding | 729 | GGGTTCCTGCTTGGGGTG | 70 |
| 18693 | Coding | 758 | GTCGGGAAAATTGATCTC | 71 |
| 18694 | Coding | 754 | GATCGTCGGGAAAATTGA | 72 |
| 18695 | Coding | 765 | GGAGCCAGGAAGATCGTC | 73 |
| 18696 | Coding | 766 | TGGAGCCAGGAAGATCGT | 74 |
| 18697 | Coding | 780 | TGGAGCAGCAGTGTTGGA | 75 |
| 18698 | Coding | 796 | GTAAAGTCTCCTGCACTG | 76 |
| 18699 | Coding | 806 | TGGCATCCATGTAAAGTC | 77 |
| 18700 | Coding | 810 | CGGTTGGCATCCATGTAA | 78 |
| 18701 | Coding | 834 | CTCTTTGCCATCCTCCTG | 79 |
| 18702 | Coding | 861 | CTGTCTCTCCTGCACTGA | 80 |
| 18703 | Stop | 873 | GGTGCAGCCTCACTGTCT | 81 |
| 18704 | 3' UTR | 910 | AACTGCCTGTTTGCCCAC | 82 |

TABLE 1-continued

Antisense sequences targeted to human CD40 mRNA

| ISIS# | TARGET REGION | TARGET SITE[1] | SEQUENCE | SEQ ID NO. |
|---|---|---|---|---|
| 18705 | 3' UTR | 954 | CTTCTGCCTGCACCCCTG | 83 |
| 18706 | 3' UTR | 976 | ACTGACTGGGCATAGCTC | 84 |

[1]Target sites are indicated by the 5' most nucleotide to which the oligonucleotide hybridizes on the CD40 mRNA sequence. Nucleotide numbers are as given in the sequence source reference (Genbank accession no. X60592, incorporated herein as SEQ ID NO: 85). Target regions on the CD40 mRNA are also indicated.

Example 10

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following four cell types are provided for illustrative purposes, but other cell types can be routinely used.

T-24 cells:

The transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in real-time quantitative polymerase chain reaction (PCR).

For Northern blotting or other analysis, cells may be seeded onto 100 mm or other standard tissue culture plates and treated similarly, using appropriate volumes of medium and oligonucleotide.

A549 cells:

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 μg/mL (Gibco/Life Technologies, Gaithersburg, Md.). Cells were routinely passaged by trysinization and dilution when they reached 90% confluence.

NHDF cells:

Human neonatal dermal fibroblast (NHDF)cells were obtained from the Clonetics Corporation (Walkersville, Md.). NHDFs were routinely maintained in Fibroblast Growth Medium (Clonetics Corporation, Walkersville, Md.) as recommended by the supplier. Cells were maintained for up to 10 passages as recommended by the supplier.

HEK cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cell were routinely maintained for up to 10 passages as recommended by the supplier.

Treatment with antisense compounds:

When cells reached 80% confluency, they were treated with oligonucleotide. For cells grown in 96-well plates, wells were washed once with 200 μl Opti-MEM™-1 reduced-serum medium (Gibco BRL) and then treated with 130 μl of Opti-MEM™-1 containing 3.75 μg/mL LIPOFECTIN™ (Gibco BRL) and the desired oligonucleotide at a final concentration of 150 nM. After 4 hours of treatment, the medium was replaced with fresh medium. Cells were harvested 16 hours after oligonucleotide treatment.

Example 11

Analysis of Oligonucleotide Inhibition of CD40 Expression

Antisense modulation of CD40 expression can be assayed in a variety of ways known in the art. For example, CD40 mRNA levels can be quantitated by, e.g., Northern blot analysis, competitive PCR, or real-time PCR. Real-time quantitative PCR is presently preferred. RNA analysis can be performed on total cellular RNA or poly(A)+ mRNA. For real-time quantitative PCR, poly(A)+ mRNA is preferred. Methods of RNA isolation are taught in, for example, Ausubel, F. M. et al., Current Protocols in Molecular Biology, Volume 1, pp.4.1.1–4.2.9 and 4.5.1–4.5.3, John Wiley & Sons, Inc., (1993). Northern blot analysis is routine in the art and is taught in, for example, Ausubel, F. M. et al., Current Protocols in Molecular Biology, Volume 1, pp. 4.2.1–4.2.9, John Wiley & Sons, Inc., (1996). Real-time quantitative polymerase chain reaction (PCR) can be conveniently accomplished using the commercially available ABI PRISM™ 7700 Sequence Detection System, available from PE-Applied Biosystems, Foster City, Calif. and used according to manufacturer's instructions. Other methods of PCR are also known in the art.

CD40 protein levels can be quantitated in a variety of ways well known in the art, such as immunoprecipitation, Western blot analysis (immunoblotting), ELISA or fluorescence-activated cell sorting (FACS). Antibodies directed to CD40 can be identified and obtained from a variety of sources, such as those identified in the MSRS catalog of antibodies, (Aerie Corporation, Birmingham, Mich.), or can be prepared via conventional antibody generation methods. Methods for preparation of polyclonal antisera are taught in, for example, Ausubel, F. M. et al., Current Protocols in Molecular Biology, Volume 2, pp. 11.12.1–11.12.9, John Wiley & Sons, Inc., (1997). Preparation of monoclonal antibodies is taught in, for example, Ausubel, F. M. et al., Current Protocols in Molecular Biology, Volume 2, pp. 11.4.1–11.11.5, John Wiley & Sons, Inc., (1997)

Immunoprecipitation methods are standard in the art and can be found at, for example, Ausubel, F. M. et al., Current Protocols in Molecular Biology, Volume 2, pp. 10.16.1–10.16.11, John Wiley & Sons, Inc., (1998). Western blot (immunoblot) analysis is standard in the art and can be found at, for example, Ausubel, F. M. et al., Current Protocols in Molecular Biology, Volume 2, pp. 10.8.1–10.8.21, John Wiley & Sons, Inc., (1997). Enzyme-linked immunosorbent assays (ELISA) are standard in the art and can be found at, for example, Ausubel, F. M. et al., Current Protocols in Molecular Biology, Volume 2, pp. 11.2.1–11.2.22, John Wiley & Sons, Inc., (1991).

Example 12

Poly(A)+ mRNA Isolation

Poly(A)+ mRNA was isolated according to Miura et al., *Clin. Chem.*, 42, 1758 (1996). Other methods for poly(A)+ mRNA isolation are taught in, for example, Ausubel, F. M. et al., Current Protocols in Molecular Biology, Volume 1, pp. 4.5.1–4.5.3, John Wiley & Sons, Inc., (1993). Briefly, for cells grown on 96-well plates, growth medium was removed from the cells and each well was washed with 200 μl cold PBS. 60 μl lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μl of lysate was transferred to Oligo d(T) coated 96-well plates (AGCT Inc., Irvine Calif.). Plates were incubated for 60 minutes at room temperature, washed 3 times with 200 μl of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μl of elution buffer (5 mM Tris-HCl pH 7.6), preheated to 70° C. was added to each well, the plate was incubated on a 90° hot plate for 5 minutes, and the eluate was then transferred to a fresh 96-well plate.

Cells grown on 100 mm or other standard plates may be treated similarly, using appropriate volumes of all solutions.

Example 13

Northern Blot Analysis of CD40 mRNA Levels

Eighteen hours after oligonucleotide treatment monolayers were washed twice with cold PBS and lysed in 0.5 mL RNAzol™ (TEL-TEST "B" Inc., Friendswood, Tex.). Total RNA was prepared following manufacturer's recommended protocols. Approximately ten μg of total RNA was fractionated by electrophoresis through 1.2% agarose gels containing 1.1% formaldehyde using a MOPS buffer system (Life Technologies, Inc., Rockville, Md.). RNA was transferred from the gel to Hybond™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a Stratalinker™ UV Crosslinker 2400 (Stratagene, Inc, La Jolla, Calif.).

Membranes were probed using QuickHyb™ hybridization solution (Stratagene, La Jolla, Calif.) using manufacturer's recommendations for stringent conditions with a CD40 specific probe prepared by PCR using the forward primer CAGAGTTCACTGAAACGGAATGC (SEQ ID No. 86) and the reverse primer GGTGGCAGTGTGTCTCTCT-GTTC (SEQ ID No. 87). To normalize for variations in loading and transfer efficiency membranes were stripped and probed for glyceraldehyde-3-phosphate dehydrogenase (G3PDH) RNA (Clontech, Palo Alto, Calif.). Hybridized membranes were visualized and quantitated using a PhosphorImager™ and ImageQuant Software V3.3 (Molecular Dynamics, Sunnyvale, Calif.). Data was normalized to G3PDH levels in untreated controls.

Example 14

Real-time Quantitative PCR Analysis of CD40 mRNA Levels

Quantitation of CD40 mRNA levels was conducted by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE or FAM, PE-Applied Biosystems, Foster City, Calif.) is attached to the 5' end of the probe and a quencher dye (e.g., TAMRA, PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular (six-second) intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

PCR reagents were obtained from PE-Applied Biosystems, Foster City, Calif. Reverse transcriptase PCR reactions were carried out by adding 25 μl PCR cocktail (1× Taqman™ buffer A, 5.5 mM MgCl$_2$, 300 μM each of dATP, dCTP and dGTP, 600 μM of dUTP, 100 nM each of forward primer, reverse primer, and probe, 20 units RNAse inhibitor, 1.25 units AmpliTaq Gold™, and 12.5 units Moloney Murine Leukemia Virus (MuLV) Reverse Transcriptase to 96 well plates containing 25 μl poly(A) mRNA solution. The RT reaction was carried out by incubation for 30 minutes at 48° C. following a 10 minute incubation at 95° C. to activate the AmpliTaq Gold™, 40 cycles of a two-step PCR protocol were carried out: 95° C. for 15 seconds (denaturation) followed by 60° C. for one minute (annealing/extension).

For CD40, the PCR primers were: forward primer: CAGAGTTCACTGAAACGGAATGC (SEQ ID No. 86) reverse primer: GGTGGCAGTGTGTCTCTCTGTTC (SEQ ID No. 87) and the PCR probe was: FAM-TTCCTTGCGGTGAAAGCGAATTCCT-TAMRA (SEQ ID No. 88) where FAM (PE-Applied Biosystems, Foster City, Calif.) is the fluorescent reporter dye) and TAMRA (PE-Applied Biosystems, Foster City, Calif.) is the quencher dye.

For GAPDH the PCR primers were: forward primer: GAAGGTGAAGGTCGGAGTC (SEQ ID No. 89) reverse primer: GAAGATGGTGATGGGATTTC (SEQ ID No. 90) and the PCR probe was: 5' JOE-CAAGCTTCCCGTTCTCAGCC- TAMRA 3' (SEQ ID No. 91) where JOE (PE-Applied Biosystems, Foster City, Calif.) is the fluorescent reporter dye) and TAMRA (PE-Applied Biosystems, Foster City, Calif.) is the quencher dye.

Example 15

Western Blot Analysis of CD40 Protein Levels

Western blot analysis (immunoblot analysis) is carried out using standard methods. Cells are harvested 16–20 hr after oligonucleotide treatment, washed once with PBS, suspended in Laemmli buffer (100 μl/well), boiled for 5 minutes and loaded on a 16% SDS-PAGE gel. Gels are run for 1.5 hours at 150 V, and transferred to membrane for western blotting. Appropriate primary antibody directed to CD40 is used, with a radiolabelled or fluorescently labeled secondary

Example 16

Antisense Inhibition of CD40 Expression by Phosphorothioate Oligodeoxynucleotides In accordance with the present invention, a series of oligonucleotides were designed to target different regions of the human CD40 mRNA, using published sequences [Stamenkovic et al., *EMBO J.*, 8, 1403 (1989); GenBank accession number X60592, incorporated herein as SEQ ID NO: 85]. The oligonucleotides are shown in Table 2. Target sites are indicated by the 5' most nucleotide to which the oligonucleotide hybridizes on the CD40 mRNA sequence. Nucleotide numbers are as given in the sequence source reference (Genbank accession no. X60592, incorporated herein as SEQ ID NO: 85). All compounds in Table 2 are oligodeoxynucleotides with phosphorothioate backbones (internucleoside linkages) throughout. The compounds were analyzed for effect on CD40 mRNA levels by real-time PCR quantitation of RNA as described in Example 14. Data are averages from three experiments.

TABLE 2

Inhibition of CD40 mRNA levels by phosphorothioate oligodeoxynucleotides

| ISIS# | TARGET REGION | TARGET SITE | SEQUENCE | % INHIB. | SEQ ID NO. |
|---|---|---|---|---|---|
| 18623 | 5' UTR | 18 | CCAGGCGGCAGGACCACT | 30.71 | 1 |
| 18624 | 5' UTR | 20 | GACCAGGCGGCAGGACCA | 28.09 | 2 |
| 18625 | 5' UTR | 26 | AGGTGAGACCAGGCGGCA | 21.89 | 3 |
| 18626 | AUG | 48 | CAGAGGCAGACGAACCAT | 0.00 | 4 |
| 18627 | Coding | 49 | GCAGAGGCAGACGAACCA | 0.00 | 5 |
| 18628 | Coding | 73 | GCAAGCAGCCCCAGAGGA | 0.00 | 6 |
| 18629 | Coding | 78 | GGTCAGCAAGCAGCCCCA | 29.96 | 7 |
| 18630 | Coding | 84 | GACAGCGGTCAGCAAGCA | 0.00 | 8 |
| 18631 | Coding | 88 | GATGGACAGCGGTCAGCA | 0.00 | 9 |
| 18632 | Coding | 92 | TCTGGATGGACAGCGGTC | 0.00 | 10 |
| 18633 | Coding | 98 | GGTGGTTCTGGATGGACA | 0.00 | 11 |
| 18634 | Coding | 101 | GTGGGTGGTTCTGGATGG | 0.00 | 12 |
| 18635 | Coding | 104 | GCAGTGGGTGGTTCTGGA | 0.00 | 13 |
| 18636 | Coding | 152 | CACAAAGAACAGCACTGA | 0.00 | 14 |
| 18637 | Coding | 156 | CTGGCACAAAGAACAGCA | 0.00 | 15 |
| 18638 | Coding | 162 | TCCTGGCTGGCACAAAGA | 0.00 | 16 |
| 18639 | Coding | 165 | CTGTCCTGGCTGGCACAA | 4.99 | 17 |
| 18640 | Coding | 176 | CTCACCAGTTTCTGTCCT | 0.00 | 18 |
| 18641 | Coding | 179 | TCACTCACCAGTTTCTGT | 0.00 | 19 |
| 18642 | Coding | 185 | GTGCAGTCACTCACCAGT | 0.00 | 20 |
| 18643 | Coding | 190 | ACTCTGTGCAGTCACTCA | 0.00 | 21 |
| 18644 | Coding | 196 | CAGTGAACTCTGTGCAGT | 5.30 | 22 |
| 18645 | Coding | 205 | ATTCCGTTTCAGTGAACT | 0.00 | 23 |
| 18646 | Coding | 211 | GAAGGCATTCCGTTTCAG | 9.00 | 24 |
| 18647 | Coding | 222 | TTCACCGCAAGGAAGGCA | 0.00 | 25 |
| 18648 | Coding | 250 | CTCTGTTCCAGGTGTCTA | 0.00 | 26 |
| 18649 | Coding | 267 | CTGGTGGCAGTGTGTCTC | 0.00 | 27 |
| 18650 | Coding | 286 | TGGGGTCGCAGTATTTGT | 0.00 | 28 |
| 18651 | Coding | 289 | GGTTGGGGTCGCAGTATT | 0.00 | 29 |
| 18652 | Coding | 292 | CTAGGTTGGGGTCGCAGT | 0.00 | 30 |
| 18653 | Coding | 318 | GGTGCCCTTCTGCTGGAC | 19.67 | 31 |
| 18654 | Coding | 322 | CTGAGGTGCCCTTCTGCT | 15.63 | 32 |
| 18655 | Coding | 332 | GTGTCTGTTTCTGAGGTG | 0.00 | 33 |
| 18656 | Coding | 334 | TGGTGTCTGTTTCTGAGG | 0.00 | 34 |
| 18657 | Coding | 345 | ACAGGTGCAGATGGTGTC | 0.00 | 35 |
| 18658 | Coding | 348 | TTCACAGGTGCAGATGGT | 0.00 | 36 |
| 18659 | Coding | 360 | GTGCCAGCCTTCTTCACA | 5.67 | 37 |
| 18660 | Coding | 364 | TACAGTGCCAGCCTTCTT | 7.80 | 38 |
| 18661 | Coding | 391 | GGACACAGCTCTCACAGG | 0.00 | 39 |
| 18662 | Coding | 395 | TGCAGGACACAGCTCTCA | 0.00 | 40 |
| 18663 | Coding | 401 | GAGCGGTGCAGGACACAG | 0.00 | 41 |
| 18664 | Coding | 416 | AAGCCGGGCGAGCATGAG | 0.00 | 42 |
| 18665 | Coding | 432 | AATCTGCTTGACCCCAAA | 5.59 | 43 |
| 18666 | Coding | 446 | GAAACCCCTGTAGCAATC | 0.10 | 44 |
| 18667 | Coding | 452 | GTATCAGAAACCCCTGTA | 0.00 | 45 |
| 18668 | Coding | 463 | GCTCGCAGATGGTATCAG | 0.00 | 46 |
| 18669 | Coding | 468 | GCAGGGCTCGCAGATGGT | 34.05 | 47 |
| 18670 | Coding | 471 | TGGGCAGGGCTCGCAGAT | 0.00 | 48 |
| 18671 | Coding | 474 | GACTGGGCAGGGCTCGCA | 2.71 | 49 |
| 18672 | Coding | 490 | CATTGGAGAAGAAGCCGA | 0.00 | 50 |
| 18673 | Coding | 497 | GATGACACATTGGAGAAG | 0.00 | 51 |
| 18674 | Coding | 500 | GCAGATGACACATTGGAG | 0.00 | 52 |
| 18675 | Coding | 506 | TCGAAAGCAGATGACACA | 0.00 | 53 |
| 18676 | Coding | 524 | GTCCAAGGGTGACATTTT | 8.01 | 54 |
| 18677 | Coding | 532 | CACAGCTTGTCCAAGGGT | 0.00 | 55 |
| 18678 | Coding | 539 | TTGGTCTCACAGCTTGTC | 0.00 | 56 |
| 18679 | Coding | 546 | CAGGTCTTTGGTCTCACA | 6.98 | 57 |

TABLE 2-continued

Inhibition of CD40 mRNA levels by phosphorothioate oligodeoxynucleotides

| ISIS# | TARGET REGION | TARGET SITE | SEQUENCE | % INHIB. | SEQ ID NO. |
|---|---|---|---|---|---|
| 18680 | Coding | 558 | CTGTTGCACAACCAGGTC | 18.76 | 58 |
| 18681 | Coding | 570 | GTTTGTGCCTGCCTGTTG | 2.43 | 59 |
| 18682 | Coding | 575 | GTCTTGTTTGTGCCTGCC | 0.00 | 60 |
| 18683 | Coding | 590 | CCACAGACAACATCAGTC | 0.00 | 61 |
| 18684 | Coding | 597 | CTGGGGACCACAGACAAC | 0.00 | 62 |
| 18685 | Coding | 607 | TCAGCCGATCCTGGGGAC | 0.00 | 63 |
| 18686 | Coding | 621 | CACCACCAGGGCTCTCAG | 23.31 | 64 |
| 18687 | Coding | 626 | GGGATCACCACCAGGGCT | 0.00 | 65 |
| 18688 | Coding | 657 | GAGGATGGCAAACAGGAT | 0.00 | 66 |
| 18689 | Coding | 668 | ACCAGCACCAAGAGGATG | 0.00 | 67 |
| 18690 | Coding | 679 | TTTTGATAAAGACCAGCA | 0.00 | 68 |
| 18691 | Coding | 703 | TATTGGTTGGCTTCTTGG | 0.00 | 69 |
| 18692 | Coding | 729 | GGGTTCCTGCTTGGGGTG | 0.00 | 70 |
| 18693 | Coding | 750 | GTCGGGAAAATTGATCTC | 0.00 | 71 |
| 18694 | Coding | 754 | GATCGTCGGGAAAATTGA | 0.00 | 72 |
| 18695 | Coding | 765 | GGAGCCAGGAAGATCGTC | 0.00 | 73 |
| 18696 | Coding | 766 | TGGAGCCAGGAAGATCGT | 0.00 | 74 |
| 18697 | Coding | 780 | TGGAGCAGCAGTGTTGGA | 0.00 | 75 |
| 18698 | Coding | 796 | GTAAAGTCTCCTGCACTG | 0.00 | 76 |
| 18699 | Coding | 806 | TGGCATCCATGTAAAGTC | 0.00 | 77 |
| 18700 | Coding | 810 | CGGTTGGCATCCATGTAA | 0.00 | 78 |
| 18701 | Coding | 834 | CTCTTTGCCATCCTCCTG | 4.38 | 79 |
| 18702 | Coding | 861 | CTGTCTCTCCTGCACTGA | 0.00 | 80 |
| 18703 | Stop | 873 | GGTGCAGCCTCACTGTCT | 0.00 | 81 |
| 18704 | 3' UTR | 910 | AACTGCCTGTTTGCCCAC | 33.89 | 82 |
| 18705 | 3' UTR | 954 | CTTCTGCCTGCACCCCTG | 0.00 | 83 |
| 18706 | 3' UTR | 976 | ACTGACTGGGCATAGCTC | 0.00 | 84 |

As shown in Table 2, SEQ ID NOs 1, 2, 7, 47 and 82 demonstrated at least 25% inhibition of CD40 expression in this assay and are therefore preferred.

Example 17

Antisense Inhibition of CD40 Expression by Phosphorothioate 2'-MOE Gapmer Oligonucleotides In accordance with the present invention, a second series of oligonucleotides targeted to human CD40 were synthesized. The oligonucleotides are shown in Table 3. Target sites are indicated by nucleotide numbers, as given in the sequence source reference (Stamenkovic et al., *EMBO J.*, 8, 1403 (1989); Genbank accession no. X60592), to which the oligonucleotide binds.

All compounds in Table 3 are chimeric oligonucleotides ("gapmers") 18 nucleotides in length, composed of a central "gap" region consisting of ten 2'-deoxynucleotides, which is flanked on both sides (5' and 3' directions) by four-nucleotide "wings." The wings are composed of 2'-methoxyethyl (2'-MOE)nucleotides. The internucleoside (backbone) linkages are phosphorothioate (P=S) throughout the oligonucleotide. Cytidine residues in the 2'-MOE wings are 5-methylcytidines.

Data were obtained by real-time quantitative PCR as described in Example 14 and are averaged from three experiments. "ND" indicates a value was not determined.

TABLE 3

Inhibition of CD40 mRNA levels by chimeric phosphorothioate oligonucleotides having 2'-MOE wings and a deoxy gap

| ISIS# | TARGET REGION | TARGET SITE | SEQUENCE | % Inhibition | SEQ ID NO. |
|---|---|---|---|---|---|
| 19211 | 5' UTR | 18 | CCAGGCGGCAGGACCACT | 75.71 | 1 |
| 19212 | 5' UTR | 20 | GACCAGGCGGCAGGACCA | 77.23 | 2 |
| 19213 | 5' UTR | 26 | AGGTGAGACCAGGCGGCA | 80.82 | 3 |
| 19214 | AUG | 48 | CAGAGGCAGACGAACCAT | 23.68 | 4 |
| 19215 | Coding | 49 | GCAGAGGCAGACGAACCA | 45.97 | 5 |
| 19216 | Coding | 73 | GCAAGCAGCCCCAGAGGA | 65.80 | 6 |
| 19217 | Coding | 78 | GGTCAGCAAGCAGCCCCA | 74.73 | 7 |
| 19218 | Coding | 84 | GACAGCGGTCAGCAAGCA | 67.21 | 8 |
| 19219 | Coding | 88 | GATGGACAGCGGTCAGCA | 65.14 | 9 |
| 19220 | Coding | 92 | TCTGGATGGACAGCGGTC | 78.71 | 10 |
| 19221 | Coding | 98 | GGTGGTTCTGGATGGACA | 81.33 | 11 |
| 19222 | Coding | 101 | GTGGGTGGTTCTGGATGG | 57.79 | 12 |
| 19223 | Coding | 104 | GCAGTGGGTGGTTCTGGA | 73.70 | 13 |
| 19224 | Coding | 152 | CACAAAGAACAGCACTGA | 40.25 | 14 |
| 19225 | Coding | 156 | CTGGCACAAAGAACAGCA | 60.11 | 15 |

TABLE 3-continued

Inhibition of CD40 mRNA levels by chimeric phosphorothioate oligonucleotides having 2'-MOE wings and a deoxy gap

| ISIS# | TARGET REGION | TARGET SITE | SEQUENCE | % Inhibition | SEQ ID NO. |
|---|---|---|---|---|---|
| 19226 | Coding | 162 | TCCTGGCTGGCACAAAGA | 10.18 | 16 |
| 19227 | Coding | 165 | CTGTCCTGGCTGGCACAA | 24.37 | 17 |
| 19228 | Coding | 176 | CTCACCAGTTTCTGTCCT | 22.30 | 18 |
| 19229 | Coding | 179 | TCACTCACCAGTTTCTGT | 40.64 | 19 |
| 19230 | Coding | 185 | GTGCAGTCACTCACCAGT | 82.04 | 20 |
| 19231 | Coding | 190 | ACTCTGTGCAGTCACTCA | 37.59 | 21 |
| 19232 | Coding | 196 | CAGTGAACTCTGTGCAGT | 40.26 | 22 |
| 19233 | Coding | 205 | ATTCCGTTTCAGTGAACT | 56.03 | 23 |
| 19234 | Coding | 211 | GAAGGCATTCCGTTTCAG | 32.21 | 24 |
| 19235 | Coding | 222 | TTCACCGCAAGGAAGGCA | 61.03 | 25 |
| 19236 | Coding | 250 | CTCTGTTCCAGGTGTCTA | 62.19 | 26 |
| 19237 | Coding | 267 | CTGGTGGCAGTGTGTCTC | 70.32 | 27 |
| 19238 | Coding | 286 | TGGGGTCGCAGTATTTGT | 0.00 | 28 |
| 19239 | Coding | 289 | GGTTGGGGTCGCAGTATT | 19.40 | 29 |
| 19240 | Coding | 292 | CTAGGTTGGGGTCGCAGT | 36.32 | 30 |
| 19241 | Coding | 318 | GGTGCCCTTCTGCTGGAC | 78.91 | 31 |
| 19242 | Coding | 322 | CTGAGGTGCCCTTCTGCT | 69.84 | 32 |
| 19243 | Coding | 332 | GTGTCTGTTTCTGAGGTG | 63.32 | 33 |
| 19244 | Coding | 334 | TGGTGTCTGTTTCTGAGG | 42.83 | 34 |
| 19245 | Coding | 345 | ACAGGTGCAGATGGTGTC | 73.31 | 35 |
| 19246 | Coding | 348 | TTCACAGGTGCAGATGGT | 47.72 | 36 |
| 19247 | Coding | 360 | GTGCCAGCCTTCTTCACA | 61.32 | 37 |
| 19248 | Coding | 364 | TACAGTGCCAGCCTTCTT | 46.82 | 38 |
| 19249 | Coding | 391 | GGACACAGCTCTCACAGG | 0.00 | 39 |
| 19250 | Coding | 395 | TGCAGGACACAGCTCTCA | 52.05 | 40 |
| 19251 | Coding | 401 | GAGCGGTGCAGGACACAG | 50.15 | 41 |
| 19252 | Coding | 416 | AAGCCGGGCGAGCATGAG | 32.36 | 42 |
| 19253 | Coding | 432 | AATCTGCTTGACCCCAAA | 0.00 | 43 |
| 19254 | Coding | 446 | GAAACCCTGTAGCAATC | 0.00 | 44 |
| 19255 | Coding | 452 | GTATCAGAAACCCCTGTA | 36.13 | 45 |
| 19256 | Coding | 463 | GCTCGCAGATGGTATCAG | 64.65 | 46 |
| 19257 | Coding | 468 | GCAGGGCTCGCAGATGGT | 74.95 | 47 |
| 19258 | Coding | 471 | TGGGCAGGGCTCGCAGAT | 0.00 | 48 |
| 19259 | Coding | 474 | GACTGGGCAGGGCTCGCA | 82.00 | 49 |
| 19260 | Coding | 490 | CATTGGAGAAGAAGCCGA | 41.31 | 50 |
| 19261 | Coding | 497 | GATGACACATTGGAGAAG | 13.81 | 5i |
| 19262 | Coding | 500 | GCAGATGACACATTGGAG | 78.48 | 52 |
| 19263 | Coding | 506 | TCGAAAGCAGATGACACA | 59.28 | 53 |
| 19264 | Coding | 524 | GTCCAAGGGTGACATTTT | 70.99 | 54 |
| 19265 | Coding | 532 | CACAGCTTGTCCAAGGGT | 0.00 | 55 |
| 19266 | Coding | 539 | TTGGTCTCACAGCTTGTC | 45.92 | 56 |
| 19267 | Coding | 546 | CAGGTCTTTGGTCTCACA | 63.95 | 57 |
| 19268 | Coding | 558 | CTGTTGCACAACCAGGTC | 82.32 | 58 |
| 19269 | Coding | 570 | GTTTGTGCCTGCCTGTTG | 70.10 | 59 |
| 19270 | Coding | 575 | GTCTTGTTTGTGCCTGCC | 68.95 | 60 |
| 19271 | Coding | 590 | CCACAGACAACATCAGTC | 11.22 | 61 |
| 19272 | Coding | 597 | CTGGGGACCACAGACAAC | 9.04 | 62 |
| 19273 | Coding | 607 | TCAGCCGATCCTGGGGAC | 0.00 | 63 |
| 19274 | Coding | 621 | CACCACCAGGGCTCTCAG | 23.08 | 64 |
| 19275 | Coding | 626 | GGGATCACCACCAGGGCT | 57.94 | 65 |
| 19276 | Coding | 657 | GAGGATGGCAAACAGGAT | 49.14 | 66 |
| 19277 | Coding | 668 | ACCAGCACCAAGAGGATG | ND | 67 |
| 19278 | Coding | 679 | TTTTGATAAAGACCAGCA | 30.58 | 68 |
| 19279 | Coding | 703 | TATTGGTTGGCTTCTTGG | 49.26 | 69 |
| 19280 | Coding | 729 | GGGTTCCTGCTTGGGGTG | 13.95 | 70 |
| 19281 | Coding | 750 | GTCGGGAAAATTGATCTC | 54.78 | 71 |
| 19282 | Coding | 754 | GATCGTCGGGAAAATTGA | 0.00 | 72 |
| 19283 | Coding | 765 | GGAGCCAGGAAGATCGTC | 69.47 | 73 |
| 19284 | Coding | 766 | TGGAGCCAGGAAGATCGT | 54.48 | 74 |
| 19285 | Coding | 780 | TGGAGCAGCAGTGTTGGA | 15.17 | 75 |
| 19286 | Coding | 796 | GTAAAGTCTCCTGCACTG | 30.62 | 76 |
| 19287 | Coding | 806 | TGGCATCCATGTAAAGTC | 65.03 | 77 |
| 19288 | Coding | 810 | CGGTTGGCATCCATGTAA | 34.49 | 78 |
| 19289 | Coding | 834 | CTCTTTGCCATCCTCCTG | 41.84 | 79 |
| 19290 | Coding | 861 | CTGTCTCTCCTGCACTGA | 25.68 | 80 |
| 19291 | Stop | 873 | GGTGCAGCCTCACTGTCT | 76.27 | 81 |
| 19292 | 3' UTR | 910 | AACTGCCTGTTTGCCCAC | 63.34 | 82 |
| 19293 | 3' UTR | 954 | CTTCTGCCTGCACCCCTG | 0.00 | 83 |
| 19294 | 3' UTR | 976 | ACTGACTGGGCATAGCTC | 11.55 | 84 |

As shown in Table 3, SEQ ID NO: 1, 2, 3, 6, 7, 8, 9, 10, 11, 12, 13, 15, 20, 23, 25, 26, 27, 31, 32, 33, 35, 37, 40, 41, 46, 47, 49, 52, 53, 54, 57, 58, 59, 60, 65, 71, 73, 74, 77, 81 and 82 demonstrated at least 50% inhibition of CD40 expression in this experiment and are therefore preferred.

Example 18

Correlation of Quantitative Real-time PCR Measurements of RNA Levels with Northern Analysis of RNA Levels The reduction of CD40 mRNA levels by the oligonucleotide compounds in Tables 2 and 3 was also demonstrated by Northern blot analysis of CD40 mRNA from oligonucleotide treated cells, as described in Example 13. The RNA measurements made by Northern analysis were compared to the RNA measurements obtained using quantitative real-time PCR, using averaged data from three experiments in each case.

When the phosphorothioate oligodeoxynucleotides shown in Table 2 were tested by Northern blot analysis, SEQ ID Nos 1, 2, 3, 7, 25, 31, 32, 37, 43, 47, 58, 64 and 82 were determined to reduce CD40 mRNA levels by at least 75% and are therefore preferred. Of these, SEQ ID Nos 1, 64 and 82 reduced CD40 mRNA levels by at least 80%.

The correlation coefficient for the results of quantitative real-time PCR vs. Northern blot analysis for the phosphorothioate oligodeoxynucleotides was found to be 0.67.

When the phosphorothioate 2'-MOE chimeric oligonucleotides shown in Table 3 were tested by Northern blot analysis, SEQ ID Nos 1, 2, 3, 5, 7, 10, 20, 25, 26, 27, 31, 32, 33, 35, 37, 40, 46, 47, 49, 52, 54, 58, 59, 60, 73, 81 and 82 were determined to reduce CD40 mRNA levels by at least 90% and are therefore preferred. Of these, SEQ ID Nos 1, 2, 20, 31 and 58 reduced CD40 mRNA levels by at least 95%.

The correlation coefficient for quantitative real-time PCR vs Northern blot results for the phosphorothioate 2'-MOE chimeric oligonucleotides was 0.78.

Example 19

Oligonucleotide-Sensitive Sites of the CD40 Target Nucleic Acid

As the data presented in the preceding examples shows, several sequences were present in preferred compounds of two distinct oligonucleotide chemistries. Specifically, compounds having SEQ ID NOS: 1, 2, 7, 47 and 82 are preferred in both instances. These compounds are believed to define accessible sites of the target nucleic acid to various antisense compositions and are therefore preferred. For example, SEQ ID NOS: 1 and 2 overlap each other and both map to the 5-untranslated region (5'-UTR) of CD40. Accordingly, this region of CD40 is particularly preferred for modulation via sequence-based technologies. Similarly, SEQ ID NOS: 7 and 47 map to the open reading frame of CD40, whereas SEQ ID NO: 82 maps to the 3'-untranslated region (3'-UTR). Thus, the ORF and 3'-UTR of CD40 may be targeted by sequence-based technologies as well.

It has been shown, furthermore, that certain target sequences on the CD40 mRNA are particularly suitable to antisense targeting. The reverse complements of the active CD40 compounds, e.g., the sequence on the CD40 nucleic acid target to which the active antisense compounds are complementary, are easily determined by those skilled in the art and may be assembled to yield nucleotide sequences corresponding to favorable sites on the target nucleic acid. For example, when the antisense sequences shown in Tables 1–3 were mapped onto the CD40 mRNA sequence [Stamenkovic et al., *EMBO J.*, 8, 1403 (1989); GenBank accession number X60592], in some instances it was found in some cases that all the oligonucleotides targeted to a particular sequence region of CD40 (usually called a "footprint") were active. Therefore, this footprint region is particularly preferred for antisense targeting, and oligonucleotide sequences hybridizable to this footprint are preferred compounds of the invention. A library of this information is compiled and may be used by those skilled in the art in a variety of sequence-based technologies to study the molecular and biological functions of CD40 and to investigate or confirm its role in various diseases and disorders.

An example of such a compilation is shown in Table 4, in which the antisense sequences shown in Tables 1–3 are mapped onto the CD40 mRNA sequence [Stamenkovic et al., *EMBO J.*, 8, 1403 (1989); GenBank accession number X60592]. The antisense sequences (SEQ ID NO: 1, 2, 3, 6, 7, 8, 9, 10, 11, 12, 13, 15, 20, 23, 25, 26, 27, 31, 32, 33, 35, 37, 40, 41, 46, 47, 49, 52, 53, 54, 57, 58, 59, 60, 65, 71, 73, 74, 77, 81 and 82) which were determined by real-time quantitative PCR assay to be active as inhibitors of CD40 are shown in bold. Examples of "footprint" sequences on the CD40 mRNA sequence to which a series of active oligonucleotides bind are also shown in bold. These "footprint" sequences and antisense compounds binding to them (including those not shown herein) are preferred for targeting.

TABLE 4

CD40 Antisense Sequence Alignment

| SEQ ID NO: | 1 | 15 | 16 | 30 | 31 | 45 | 46 | 60 | 61 | 75 | 76 | 90 |
|---|---|---|---|---|---|---|---|---|---|---|---|---|
| 9 | ---------------- | ---------------- | ---------------- | ---------------- | ---------------- | ------------TGC |
| 8 | ---------------- | ---------------- | ---------------- | ---------------- | ---------------- | ---------TGCTTGC |
| 7 | ---------------- | ---------------- | ---------------- | ---------------- | ---------------- | --TGGGGCTGCTTGC |
| 6 | ---------------- | ---------------- | ---------------- | ---------------- | ------------TCC | TCTGGGGCTGCTTGC |
| 5 | ---------------- | ---------------- | ---------------- | ---TGGTTCGTCTGC | CTCTGC---------- | ---------------- |
| 4 | ---------------- | ---------------- | ---------------- | --ATGGTTCGTCTGC | CTCTG---------- | ---------------- |
| 3 | ---------------- | ----------TGCCG | CCTGGTCTCACCT-- | ---------------- | ---------------- | ---------------- |
| 2 | ---------------- | ----TGGTCCTGCCG | CCTGGTC-------- | ---------------- | ---------------- | ---------------- |
| 1 | ---------------- | --AGTGGTCCTGCCG | CCTGG---------- | ---------------- | ---------------- | ---------------- |
| X60592-CD40 | GCCTCGCTCGGGCGC | CCAGTGGTCCTGCCG | CCTGGTCTCACCTCG | CCATGGTTCGTCTGC | CTCTGCAGTGCGTCC | TCTGGGCTGCTTGC |

TABLE 4-continued

CD40 Antisense Sequence Alignment

SEQ ID
NO:

```
          91            105 106           120 121           135 136           150 151           165 166           180
19        ---------------   ---------------   ---------------   ---------------   ---------------   -------------AC
18        ---------------   ---------------   ---------------   ---------------   ---------------   ----------AGGAC
17        ---------------   ---------------   ---------------   ---------------   ---------------   -------------T TGTGCCAGCCAGGAC
16        ---------------   ---------------   ---------------   ---------------   ---------------   ----------TCTT TGTGCCAGCCAGGA-
15        ---------------   ---------------   ---------------   ---------------   ---------------   -----TGCTGTTCTT TGTGCCAG-------
14        ---------------   ---------------   ---------------   ---------------   ---------------   -TCAGTGCTGTTCTT TGTG-----------
13        -------------TC   CAGAACCACCCACTG   C--------------   ---------------   ---------------   ---------------
12        ----------CCATC   CAGAACCACCCAC--   ---------------   ---------------   ---------------   ---------------
11        -------TGTCCATC   CAGAACCACC-----   ---------------   ---------------   ---------------   ---------------
10        -GACCGCTGTCCATC   CAGA-----------   ---------------   ---------------   ---------------   ---------------
9         TGACCGCTGTCCATC   ---------------   ---------------   ---------------   ---------------   ---------------
8         TGACCGCTGTC----   ---------------   ---------------   ---------------   ---------------   ---------------
7         TGACC----------   ---------------   ---------------   ---------------   ---------------   ---------------
X60592-   TGACCGCTGTCCATC   CAGAACCACCCACTG   CATGCAGAGAAAAAC   AGTACCTAATAAACA   GTCAGTGCTGTTCTT   TGTGCCAGCCAGGAC
CD40

181           195 196           210 211           225 226           240 241           255 256           270
27        ---------------   ---------------   ---------------   ---------------   ---------------   -----------GAGA
26        ---------------   ---------------   ---------------   ---------------   ---------------   ---------TAGACA CCTGGAACAGAG---
25        ---------------   ---------------   ---------------   -----------TGCC   TTCCTTGCGGTGAA-   ---------------
24        ---------------   ---------------   ---------------   CTGAAACGGAATGCC   TTC------------   ---------------
23        ---------------   ---------AGTTCA   CTGAAACGGAAT---   ---------------   ---------------   ---------------
22        ---------------   ACTGCACAGAGTTCA   CTG------------   ---------------   ---------------   ---------------
21        ---------TGAGTG   ACTGCACAGAGT---   ---------------   ---------------   ---------------   ---------------
20        ----ACTGGTGAGTG   ACTGCAC--------   ---------------   ---------------   ---------------   ---------------
19        AGAAACTGGTGAGTG   A--------------   ---------------   ---------------   ---------------   ---------------
18        AGAAACTGGTGAG--   ---------------   ---------------   ---------------   ---------------   ---------------
17        AG-------------   ---------------   ---------------   ---------------   ---------------   ---------------
X60592-   AGAAACTGGTGAGTG   ACTGCACAGAGTTCA   CTGAAACGGAATGCC   TTCCTTGCGGTGAAA   GCGAATTCCTAGACA CCTGGAACAGAGAGA
CD40

271           285 286           300 301           315 316           330 331           345 346           360
37        ---------------   ---------------   ---------------   ---------------   ---------------   -------------T
36        ---------------   ---------------   ---------------   ---------------   ---------------   --ACCATCTGCACCT
35        ---------------   ---------------   ---------------   ---------------   ---------------   -G ACACCATCTGCACCT
34        ---------------   ---------------   ---------------   ---------------   ---CCTCAGAAACAG   ACACCA---------
33        ---------------   ---------------   ---------------   ---------------   -CACCTCAGAAACAG   ACAC-----------
32        ---------------   ---------------   ---------------   ---------------   ------AGCAGAAGG   GCACCTCAG------
31        ---------------   ---------------   ---------------   ---------------   --GTCCAGCAGAAGG   GCACC----------
30        ---------------   ---------------   ------ACTGCGACC   CCAACCTAG------   ---------------   ---------------
29        ---------------   ---------------   ---AATACTGCGACC   CCAACC---------   ---------------   ---------------
28        ---------------   ---------------   ACAAATACTGCGACC   CCA------------   ---------------   ---------------
27        GACACTGCGACCAG-   ---------------   ---------------   ---------------   ---------------   ---------------
X60592-   GACACTGCCACCAGC   ACAAATACTGCGACC   CCAACCTAGGGCTTC   GGGTCCAGCAGAAGG   GCACCTCAGAAACAG   ACACCATCTGCACCT
CD40

361           375 376           390 391           405 406           420 421           435 436           450
44        ---------------   ---------------   ---------------   ---------------   ---------------   ----------GATTG
43        ---------------   ---------------   ---------------   ---------------   -----------TTTG   GGGTCAAGCAGATT-
42        ---------------   ---------------   ---------------   -------CTCAT   GCTCGCCCGGCTT--   ---------------
41        ---------------   ---------------   -------CTGTG   TCCTGCACCGCTC--   ---------------   ---------------
40        ---------------   ---------------   ----TGAGAGCTGTG   TCCTGCA--------   ---------------   ---------------
39        ---------------   ---------------   CCTGTGAGAGCTGTG   TCC------------   ---------------   ---------------
38        ---AAGAAGGCTGGC   ACTGTA---------   ---------------   ---------------   ---------------   ---------------
37        GTGAAGAAGGCTGGC   AC-------------   ---------------   ---------------   ---------------   ---------------
36        GTGAA----------   ---------------   ---------------   ---------------   ---------------   ---------------
35        GT-------------   ---------------   ---------------   ---------------   ---------------   ---------------
X60592-   GTGAAGAAGGCTGGC   ACTGTACGAGTGAGG   CCTGTGAGAGCTGTG   TCCTGCACCGCTCAT   GCTCGCCCGGCTTTG   GGGTCAAGCAGATTG
CD40

451           465 466           480 481           495 496           510 511           525 526           540
56        ---------------   ---------------   ---------------   ---------------   ---------------   -------------GA
55        ---------------   ---------------   ---------------   ---------------   ---------------   -------ACCCTTGA
54        ---------------   ---------------   ---------------   ---------------   ---------------   --------AA AATGTCACCCTTGA
53        ---------------   ---------------   ---------------   ---------------   ----------TGTGT   CATCTGCTTTCGA--
52        ---------------   ---------------   ---------------   ---------------   ----CTCCAATGTGT   CATCTGC--------
51        ---------------   ---------------   ---------------   ---------CTTCTCCAATGTGT   CATC-----------   ---------------
50        ---------------   ---------------   ---------TCGGCT   TCTTCTCCAATG---   ---------------   ---------------
```

TABLE 4-continued

CD40 Antisense Sequence Alignment

```
SEQ ID
NO:
49     ---------------- -------TGCGAGC CCTGCCCAGTC---- ---------------- ---------------- ----------------
48     ---------------- -----ATCTGCGAGC CCTGCCCA------- ---------------- ---------------- ----------------
47     ---------------- --ACCATCTGCGAGC CCTGC----------- ---------------- ---------------- ----------------
46     ------------CTG ATACCATCTGCGAGC ---------------- ---------------- ---------------- ----------------
45     -TACAGGGGTTTCTG ATAC------------ ---------------- ---------------- ---------------- ----------------
44     CTACAGGGGTTTC-- ---------------- ---------------- ---------------- ---------------- ----------------
X60592- CTACAGGGGTTTCTG ATACCATCTGCGAGC CCTGCCCAGTCGGCT TCTTCTCCAATGTGT CATCTGCTTTCGAAA AATGTCACCCTTGGA
CD40

541          555 556          570 571          585 586          600 601          615 616          630
65     ---------------- ---------------- ---------------- ---------------- ---------------- ---------AGCCC
64     ---------------- ---------------- ---------------- ---------------- ---------------- -----CTGAGAGCCC
63     ---------------- ---------------- ---------------- ---------------- ------GTCCCCAGG ATCGGCTGA------
62     ---------------- ---------------- ---------------- -----------GTTG TCTGTGGTCCCAG- ----------------
61     ---------------- ---------------- ---------------- ----GACTGATGTTG TCTGTGG--------- ----------------
60     ---------------- ---------------- ----GGCAGGCACAA ACAAGAC--------- ---------------- ----------------
59     ---------------- ---------------C AACAGGCAGGCACAA AC-------------- ---------------- ----------------
58     ---------------- --GACCTGGTTGTGC AACAG----------- ---------------- ---------------- ----------------
57     -----TGTGAGACCA AAGACCTG-------- ---------------- ---------------- ---------------- ----------------
56     CAAGCTGTGAGACCA A--------------- ---------------- ---------------- ---------------- ----------------
55     CAAGCTGTG------ ---------------- ---------------- ---------------- ---------------- ----------------
54     C--------------- ---------------- ---------------- ---------------- ---------------- ----------------
X60592- CAAGCTGTGAGACCA AAGACCTGGTTGTGC AACAGGCAGGCACAA ACAAGACTGATGTTG TCTGTGGTCCCCAGG ATCGGCTGAGAGCCC
CD40

631          645 646          660 661          675 676          690 691          705 706          720
69     ---------------- ---------------- ---------------- ---------------- ---------------- ----CCA AGAAGCCAACCAATA
68     ---------------- ---------------- ---------------- ---TGCTGGTCTTTA TCAAAA---------- ----------------
67     ---------------- ---------------- -------CATCCTCT TGGTGCTGGT------ ---------------- ----------------
66     ---------------- -----------ATCC TGTTTGCCATCCTC- ---------------- ---------------- ----------------
65     TGGTGGTGATCCC-- ---------------- ---------------- ---------------- ---------------- ----------------
64     TGGTGGTG-------- ---------------- ---------------- ---------------- ---------------- ----------------
X60592- TGGTGGTGATCCCCA TCATCTTCGGGATCC TGTTTGCCATCCTCT TGGTGCTGGTCTTTA TCAAAAAGGTGGCCA AGAAGCCAACCAATA
CD40

721          735 736          750 751          765 766          780 781          795 796          810
78     ---------------- ---------------- ---------------- ---------------- ---------------- ---------------T
77     ---------------- ---------------- ---------------- ---------------- ---------------- ----------GACTT
76     ---------------- ---------------- ---------------- ---------------- ---------------- CAGTGCAGGAGACTT
75     ---------------- ---------------- ---------------- --------------T CCAACACTGCTGCTC CA--------------
74     ---------------- ---------------- ---------------- ACGATCTTCCTCGCT CCA------------- ----------------
73     ---------------- ---------------- ---------------G ACGATCTTCCTGGCT CC-------------- ----------------
72     ---------------- ---------------- ---TCAATTTTCCCG ACGATC---------- ---------------- ----------------
71     ---------------- ---------------G AGATCAATTTTCCCG AC-------------- ---------------- ----------------
70     --------CACCCCA AGCAGGAACCCC---- ---------------- ---------------- ---------------- ----------------
X60592- AGGCCCCCCACCCCA AGCAGGAACCCCAGG AGATCAATTTTCCCG ACGATCTTCCTGGCT CCAACACTGCTGCTC CAGTGCAGGAGACTT
CD40

811          825 826          840 841          855 856          870 871          885 886          900
81     ---------------- ---------------- ---------------- ---------------- --AGACAGTGAGGCT GCACC-----------
80     ---------------- ---------------- ---------------- -----TCAGTGCAGG AGAGACAG------- ----------------
79     ---------------- ---------------- -------CAGGAGG ATGGCAAAGAG---- ---------------- ----------------
78     TACATGGATGCCAAC CG-------------- ---------------- ---------------- ---------------- ----------------
77     TACATGCATGCCA-- ---------------- ---------------- ---------------- ---------------- ----------------
86     TAC------------- ---------------- ---------------- ---------------- ---------------- ----------------
X60592- TACATGGATGCCAAC CGGTCACCCAGGAGG ATGGCAAAGAGAGTC GCATCTCAGTGCAGG AGAGACAGTGAGGCT GCACCCACCCAGGAG
CD40

901          915 916          930 931          945 946          960 961          975 976          990
84     ---------------- ---------------- ---------------- ---------------- ---------------- GAGCTATGCCCAGTC
83     ---------------- ---------------- ---------------- --------CAGGGGT GCAGGCAGAAG---- ----------------
82     ---------GTGGGC AAACAGGCAGTT--- ---------------- ---------------- ---------------- ----------------
X60592- TGTGGCCACGTGGGC AAACAGGCAGTTGGC CAGAGAGCCTGGTGC TGCTGCTGCAGGGGT GCAGGCAGAAGCGGG GAGCTATGCCCAGTC
CD40

991         1004
84     AGT-----------
X60592- AGTGCCAGCCCCTC
CD40
```

What is claimed is:

1. An antisense oligonucleotide 8 to 30 nucleobases in length targeted to nucleotides 73 through 122 or nucleotides 152 through 240 or nucleotides 250 through 309 or nucleotides 318 through 381 or nucleotides 391 through 643 or nucleotides 657 through 696 or nucleotides 703 through 720 or nucleotides 729 through 746 or nucleotides 750 through 827 or nucleotides 834 through 851 or nucleotides 861 through 878 of a coding region, nucleotides 910 through 927 or nucleotides 954 through 971 or nucleotides 976 through 993 of a 3'UTR, or nucleotides 18 through 43 of a 5'UTR of a nucleic acid molecule encoding human CD40 SEQ ID NO:85, wherein said antisense oligonucleotide inhibits the expression of human CD40.

2. An antisense oligonucleotide comprising SEQ ID NO: 1, 3, 5, 6, 8, 9, 11, 12, 13, 15, 20, 23, 25, 26, 27, 31, 32, 33, 35, 37, 40, 41, 43, 46, 47, 49, 52, 53, 54, 57, 58, 59, 60, 64, 65, 71, 73, 74, 77, 81 or 82 which inhibits the expression of human CD40.

3. The antisense oligonucleotide of claim 1 which comprises at least one modified internucleoside linkage.

4. The antisense oligonucleotide of claim 3 wherein the modified internucleoside linkage is a phosphorothioate linkage.

5. The antisense oligonucleotide of claim 1 wherein the antisense oligonucleotide comprises at least one modified sugar moiety.

6. The antisense oligonucleotide of claim 5 wherein the modified sugar moiety is a 2'-O-methoxyethyl sugar moiety.

7. The antisense oligonucleotide of claim 1 wherein the antisense oligonucleotide comprises at least one modified nucleobase.

8. The antisense oligonucleotide of claim 7 wherein the modified nucleobase is a 5-methylcytosine.

9. The antisense oligonucleotide of claim 1 wherein the antisense oligonucleotide is a chimeric oligonucleotide.

10. A method of inhibiting the expression of human CD40 in human cells or tissues comprising contacting said cells or tissues in vitro with the antisense oligonucleotide of claim 1 so that expression of human CD40 is inhibited.

11. The antisense oligonucleotide of claim 2 wherein the antisense oligonucleotide comprises at least one modified internucleoside linkage.

12. The antisense oligonucleotide of claim 11 wherein the modified internucleoside linkage is a phosphorothioate linkage.

13. The antisense oligonucleotide of claim 2 wherein the antisense oligonucleotide comprises at least one modified sugar moiety.

14. The antisense oligonucleotide of claim 13 wherein the modified sugar moiety is a 2'-O-methoxyethyl sugar moiety.

15. The antisense oligonucleotide of claim 2 wherein the antisense oligonucleotide comprises at least one modified nucleobase.

16. The antisense oligonucleotide of claim 15 wherein the modified nucleobase is a 5-methylcytosine.

17. The antisense oligonucleotide of claim 2 wherein the antisense oligonucleotide is a chimeric oligonucleotide.

18. A method of inhibiting the expression of human CD40 in human cells or tissues comprising contacting said cells or tissues in vitro with the antisense oligonucleotide of claim 2 so that expression of human CD40 is inhibited.

19. An antisense oligonucleotide consisting of SEQ ID NO:2, 7 or 10 which inhibits the expression of human CD40.

* * * * *

SEQUENCE LISTING

<160> NUMBER OF SEQ ID NOS: 91

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 1
ccaggcggca ggaccact                                                 18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 2
gaccaggcgg caggacca                                                 18

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 3
aggtgagacc aggcggca                                                 18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 4
cagaggcaga cgaaccat                                                 18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 5
gcagaggcag acgaacca                                                 18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 6
gcaagcagcc ccagagga                                                 18

<210> SEQ ID NO 7
<211> LENGTH: 18

```
<212> TYPE: DNA
<213> ORGANISM: Artificial Sequence
<220> FEATURE:
<223> OTHER INFORMATION: Description of Artificial Sequence:Synthetic

<400> SEQUENCE: 7
ggtcagcaag cagcccca                                                18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 8
gacagcggtc agcaagca                                                18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 9
gatggacagc ggtcagca                                                18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 10
tctggatgga cagcggtc                                                18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 11
ggtggttctg gatggaca                                                18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 12
gtgggtggtt ctggatgg                                                18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence:Synthetic
```

-continued

```
<400> SEQUENCE: 13
gcagtgggtg gttctgga                                                    18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 14
cacaaagaac agcactga                                                    18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 15
ctggcacaaa gaacagca                                                    18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 16
tcctggctgg cacaaaga                                                    18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 17
ctgtcctggc tggcacaa                                                    18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 18
ctcaccagtt tctgtcct                                                    18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 19
tcactcacca gtttctgt                                                    18

<210> SEQ ID NO 20
<211> LENGTH: 18
```

```
<212> TYPE: DNA
<213> ORGANISM: Artificial Sequence
<220> FEATURE:
<223> OTHER INFORMATION: Description of Artificial Sequence:Synthetic

<400> SEQUENCE: 20
gtgcagtcac tcaccagt                                              18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 21
actctgtgca gtcactca                                              18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 22
cagtgaactc tgtgcagt                                              18

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 23
attccgtttc agtgaact                                              18

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 24
gaaggcattc cgtttcag                                              18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 25
ttcaccgcaa ggaaggca                                              18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence:Synthetic
```

<400> SEQUENCE: 26
ctctgttcca ggtgtcta                                                          18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 27
ctggtggcag tgtgtctc                                                          18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 28
tggggtcgca gtatttgt                                                          18

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 29
ggttggggtc gcagtatt                                                          18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 30
ctaggttggg gtcgcagt                                                          18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 31
ggtgcccttc tgctggac                                                          18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 32
ctgaggtgcc cttctgct                                                          18

<210> SEQ ID NO 33
<211> LENGTH: 18

```
<212> TYPE: DNA
<213> ORGANISM: Artificial Sequence
<220> FEATURE:
<223> OTHER INFORMATION: Description of Artificial Sequence:Synthetic

<400> SEQUENCE: 33
gtgtctgttt ctgaggtg                                              18

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 34
tggtgtctgt ttctgagg                                              18

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 35
acaggtgcag atggtgtc                                              18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 36
ttcacaggtg cagatggt                                              18

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 37
gtgccagcct tcttcaca                                              18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 38
tacagtgcca gccttctt                                              18

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence:Synthetic
```

<400> SEQUENCE: 39
ggacacagct ctcacagg                                                    18

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 40
tgcaggacac agctctca                                                    18

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 41
gagcggtgca ggacacag                                                    18

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 42
aagccgggcg agcatgag                                                    18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 43
aatctgcttg accccaaa                                                    18

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 44 gaaaccctg tagcaatc                                                     18

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 45
gtatcagaaa cccctgta                                                    18

<210> SEQ ID NO 46
<211> LENGTH: 18

```
<212> TYPE: DNA
<213> ORGANISM: Artificial Sequence
<220> FEATURE:
<223> OTHER INFORMATION: Description of Artificial Sequence:Synthetic

<400> SEQUENCE: 46
gctcgcagat ggtatcag                                              18

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 47
gcagggctcg cagatggt                                              18

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 48
tgggcagggc tcgcagat                                              18

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 49
gactgggcag ggctcgca                                              18

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 50
cattggagaa gaagccga                                              18

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 51
gatgacacat tggagaag                                              18

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence:Synthetic
```

<400> SEQUENCE: 52
gcagatgaca cattggag                                           18

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 53
tcgaaagcag atgacaca                                           18

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 54
gtccaagggt gacatttt                                           18

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 55
cacagcttgt ccaagggt                                           18

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 56
ttggtctcac agcttgtc                                           18

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 57
caggtctttg gtctcaca                                           18

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 58
ctgttgcaca accaggtc                                           18

<210> SEQ ID NO 59
<211> LENGTH: 18

```
<212> TYPE: DNA
<213> ORGANISM: Artificial Sequence
<220> FEATURE:
<223> OTHER INFORMATION: Description of Artificial Sequence:Synthetic

<400> SEQUENCE: 59
gtttgtgcct gcctgttg                                                    18

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 60
gtcttgtttg tgcctgcc                                                    18

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 61
ccacagacaa catcagtc                                                    18

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 62
ctggggacca cagacaac                                                    18

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 63
tcagccgatc ctggggac                                                    18

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 64
caccaccagg gctctcag                                                    18

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence:Synthetic
```

```
<400> SEQUENCE: 65
gggatcacca ccagggct                                              18

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 66
gaggatggca aacaggat                                              18

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 67
accagcacca agaggatg                                              18

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 68
ttttgataaa gaccagca                                              18

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 69
tattggttgg cttcttgg                                              18

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 70
gggttcctgc ttggggtg                                              18

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 71
gtcgggaaaa ttgatctc                                              18

<210> SEQ ID NO 72
<211> LENGTH: 18
```

```
<212> TYPE: DNA
<213> ORGANISM: Artificial Sequence
<220> FEATURE:
<223> OTHER INFORMATION: Description of Artificial Sequence:Synthetic

<400> SEQUENCE: 72
gatcgtcggg aaaattga                                                      18

<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 73
ggagccagga agatcgtc                                                      18

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 74
tggagccagg aagatcgt                                                      18

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 75
tggagcagca gtgttgga                                                      18

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 76
gtaaagtctc ctgcactg                                                      18

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 77
tggcatccat gtaaagtc                                                      18

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence:Synthetic
```

```
<400> SEQUENCE: 78
cggttggcat ccatgtaa                                                18

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 79
ctctttgcca tcctcctg                                                18

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 80
ctgtctctcc tgcactga                                                18

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 81
ggtgcagcct cactgtct                                                18

<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 82
aactgcctgt ttgcccac                                                18

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 83
cttctgcctg cacccctg                                                18

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence:Synthetic

<400> SEQUENCE: 84
actgactggg catagctc                                                18

<210> SEQ ID NO 85
<211> LENGTH: 1004
```

-continued

<212> TYPE: DNA
<213> ORGANISM: Artificial Sequence
<220> FEATURE:
<223> OTHER INFORMATION: Description of Artificial Sequence:Synthetic

<400> SEQUENCE: 85

```
gcctcgctcg ggcgcccagt ggtcctgccg cctggtctca cctcgccatg gttcgtctgc      60
ctctgcagtg cgtcctctgg ggctgcttgc tgaccgctgt ccatccagaa ccacccactg     120
catgcagaga aaacagtac ctaataaaca gtcagtgctg ttctttgtgc cagccaggac      180
agaaactggt gagtgactgc acagagttca ctgaaacggaa atgccttcct tgcggtgaaa    240
gcgaattcct agacacctgg aacagagaga cacactgcca ccagcacaaa tactgcgacc    300
ccaacctagg gcttcgggtc cagcagaagg gcacctcaga aacagacacc atctgcacct    360
gtgaagaagg ctggcactgt acgagtgagg cctgtgagag ctgtgtcctg caccgctcat    420
gctcgcccgg ctttggggtc aagcagattg ctacaggggt ttctgatacc atctgcgagc    480
cctgcccagt cggcttcttc tccaatgtgt catctgcttt cgaaaaatgt caccccttgga  540
caagctgtga gaccaaagac ctggttgtgc aacaggcagg cacaaacaag actgatgttg    600
tctgtggtcc ccaggatcgg ctgagagccc tggtggtgat ccccatcatc ttcgggatcc    660
tgtttgccat cctcttggtg ctggtctttta tcaaaaaggt ggccaagaag ccaaccaata    720
aggcccccca ccccaagcag gaaccccagg agatcaattt tcccgacgat cttcctggct    780
ccaacactgc tgctccagtg caggagactt tacatggatg ccaaccggtc acccaggagg    840
atggcaaaga gagtcgcatc tcagtgcagg agagacagtg aggctgcacc cacccaggag    900
tgtggccacg tgggcaaaca ggcagttggc cagagagcct ggtgctgctg ctgcaggggt    960
gcaggcagaa gcggggagct atgcccagtc agtgccagcc cctc                     1004
```

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence:Synthetic

<400> SEQUENCE: 86

```
cagagttcac tgaaacggaa tgc                                             23
```

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence:Synthetic

<400> SEQUENCE: 87

```
ggtggcagtg tgtctctctg ttc                                             23
```

<210> SEQ ID NO 88
<211> LENGTH: 25
<212> TYPE: DNA
<213> ORGANISM: Artificial Sequence
<220> FEATURE:
<223> OTHER INFORMATION: Description of Artificial Sequence:Synthetic

<400> SEQUENCE: 88

```
ttccttgcgg tgaaagcgaa ttcct                                           25
```

-continued

```
<210> SEQ ID NO 89
<211> LENGTH: 19
<212> TYPE: DNA
<213> ORGANISM: Artificial Sequence
<220> FEATURE:
<223> OTHER INFORMATION: Description of Artificial Sequence:Synthetic

<400> SEQUENCE: 89
gaaggtgaag gtcggagtc                                                        19

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 90
gaagatggtg atgggatttc                                                       20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 91
caagcttccc gttctcagcc                                                       20
```